(12) United States Patent
Qin et al.

(10) Patent No.: US 11,261,593 B2
(45) Date of Patent: Mar. 1, 2022

(54) SMART TOILET WITH AUTOMATIC URINE POSITION DETECTING SYSTEM

(71) Applicant: Shanghai Kohler Electronics, Ltd., Shanghai (CN)

(72) Inventors: Zhiyu Qin, Beijing (CN); Qintao Sun, Beijing (CN)

(73) Assignee: Shanghai Kohler Electronics, Ltd., Shanghai (CN)

( * ) Notice: Subject to any disclaimer, the term of this patent is extended or adjusted under 35 U.S.C. 154(b) by 0 days.

(21) Appl. No.: 16/925,742

(22) Filed: Jul. 10, 2020

(65) Prior Publication Data

US 2020/0407963 A1    Dec. 31, 2020

Related U.S. Application Data

(63) Continuation of application No. 16/097,229, filed as application No. PCT/CN2016/103184 on Oct. 25, 2016, now Pat. No. 10,731,326.

(30) Foreign Application Priority Data

Apr. 28, 2016    (CN) .......................... 201610273915.9

(51) Int. Cl.
| | | |
|---|---|---|
| *E03D 11/13* | (2006.01) | |
| *E03D 11/00* | (2006.01) | |
| *A61B 10/00* | (2006.01) | |
| *E03D 9/00* | (2006.01) | |

(52) U.S. Cl.
CPC ............ *E03D 11/13* (2013.01); *A61B 10/007* (2013.01); *E03D 9/00* (2013.01); *E03D 11/00* (2013.01)

(58) Field of Classification Search
CPC .......... E03D 11/13; E03D 11/00; E03D 9/00; A61B 10/007; G01J 5/0003; G05D 3/183; G01K 2213/00; G01K 13/223
See application file for complete search history.

(56) References Cited

U.S. PATENT DOCUMENTS

| | | | |
|---|---|---|---|
| 4,870,252 | A | 9/1989 | Balmer |
| 6,892,402 | B2 | 5/2005 | Lim |
| 9,756,297 | B1 | 9/2017 | Clements |
| 2005/0258258 | A1 | 11/2005 | Smiljanic |
| 2020/0407963 | A1* | 12/2020 | Qin ..................... A61B 10/007 |

FOREIGN PATENT DOCUMENTS

| | | |
|---|---|---|
| CN | 102724938 | 10/2012 |
| CN | 102995735 | 3/2013 |
| CN | 104771266 | 7/2015 |
| CN | 104840140 | 8/2015 |

(Continued)

OTHER PUBLICATIONS

International Search Report re Application No. PCT/CN2016/103219; 6 pgs.

(Continued)

*Primary Examiner* — Marcus H Taningco
(74) *Attorney, Agent, or Firm* — Foley & Lardner LLP (57) ABSTRACT

A toilet includes a module including a sensor that is configured to determine a characteristic of urine with the urine in a non-contact position with a surface of the toilet, wherein the module is configured to calculate point coordinates of the non-contact position of the urine.

20 Claims, 9 Drawing Sheets

(56) References Cited

FOREIGN PATENT DOCUMENTS

| | | |
|---|---|---|
| CN | 104963395 | 10/2015 |
| CN | 105804189 | 7/2016 |
| CN | 205604388 | 9/2016 |
| JP | 09-159441 | 6/1997 |
| JP | 2008-249672 | 10/2008 |
| JP | 2008249672 A * | 10/2008 |
| JP | 2015-114181 | 6/2015 |
| JP | 2015-178764 | 10/2015 |

OTHER PUBLICATIONS

PCT International Preliminary Report on Patentability re PCT/CN2016/103184; 5 pages.
PCT International Search Report and Written Opinion re PCT/CN2016/103184; 9 pages.
Foreign Action other than Search Report on KR 10-2018-7034096 dated Sep. 19, 2019.
Foreign Action other than Search Report on non-Foley case related to U.S. Appl. No. 16/925,742 dated Apr. 28, 2020 Second Office Action.
Foreign Action other than Search Report on non-Foley case related to U.S. Appl. No. 16/925,742 dated May 25, 2020.

* cited by examiner

SMART TOILET WITH AUTOMATIC URINE POSITION DETECTING SYSTEM

CROSS-REFERENCE TO RELATED PATENT APPLICATIONS

This application is a Continuation of U.S. patent application Ser. No. 16/097,229, filed Oct. 26, 2018, which is a U.S. National Stage of International Application No. PCT/CN2016/103184, filed Oct. 25, 2016, which claims the benefit of and priority to Chinese Patent Application No. 201610273915.9, filed Apr. 28, 2016. The entire disclosures of the foregoing applications are hereby incorporated by reference herein.

BACKGROUND

As the people's living standard continues to rise, smart toilet has gradually stepped into people's life. In addition to satisfying the comfort requirements, the smart toilet is additionally provided with a health monitoring function, such as making a health data analysis through collecting urine sample. However, cross-contamination may occur when using urine samples collected from an inner surface of the toilet, which affects the accuracy of the health data analysis. Therefore, at present, how to avoid the cross-contamination between urine samples absorbed from the inner surface of the toilet to improve the accuracy of the health data analysis has become an urgent problem to be solved.

SUMMARY

A first technical problem to be solved by the present invention is to provide a method for automatically positioning urine, used for a healthy smart toilet. In this method, the urine can be positioned while it is in the air before contacting the toilet, therefore the urine can be collected without contacting the toilet. This method prevents the cross-contamination between urine samples and improves the accuracy of the health data analysis.

The present invention uses the following technical solutions in order to solve the above-mentioned technical problems.

A method for automatically positioning urine, comprising: determining a position of the urine according to a temperature result scanned by a non-contact temperature sensor, and calculating point coordinates of the position of the urine in a toilet.

Further, the method comprises: step A: scanning and detecting temperature by sector scanning within an angle $\gamma$ using the non-contact temperature sensor arranged in a left or right side wall of the toilet, the non-contact temperature sensor is driven by a stepping motor; calculating X in point coordinates (X, Y) of the position of the urine in the toilet based on the angle with the highest temperature and tangent formula; and/or step B: scanning and detecting temperature within an angle $\delta$ by sector scanning using the non-contact temperature sensor arranged in a front or rear side wall of the toilet, the non-contact temperature sensor is driven by a stepping motor, and calculating Y in point coordinates (X, Y) of the position of the urine in the toilet based on the angle with the highest temperature and tangent formula.

Further, the step A specifically comprises: step A1: when the sensor scans within the angle $\gamma$, each time the stepping motor turns by an angle $\varphi$, the sensor reads temperature and records the highest temperature value and the turning angle $\lambda$ of the stepping motor at which the highest temperature value is read; and step A2: calculating the position of the urine each time the sensor reaches the boundary of the angle $\gamma$.

Step B specifically comprises: step B1: when the sensor scans within the angle $\delta$, each time the stepping motor turns by an angle $\theta$, the sensor reads temperature and records the highest temperature value and the turning angle $\omega$ of the stepping motor at which the highest temperature value is read; and step B2: calculating the position of the urine each time the sensor reaches the boundary of the angle $\delta$.

Further, in the step A2, the calculation method is X=(L1/COS $\mu$)*TAN($|\gamma/2-\lambda|$); wherein, L1 is the distance between the long shaft of the toilet and the central scanning point of the left or right side wall where the sensor is located, and $\mu$ is an included angle between a scanning plane of the sensor and the horizontal plane; and in the step B2, the calculation method is Y=(L2/COS $\xi$)*TAN($|\delta/2-\omega|$); wherein, L2 is the distance between the short shaft of the toilet and the central scanning point of the front or rear side wall where the sensor is located, and $\xi$ is an included angle between a scanning plane of the sensor and the horizontal plane.

Further, in the steps A1 and B1, when the sensor reads temperature, the lowest temperature value is recorded meanwhile; and in the steps A2 and B2, each time the sensor reaches the boundary, a temperature difference between the highest temperature and the lowest temperature is calculated, and if the temperature difference is greater than a set temperature difference threshold, the position of the urine is calculated.

Further, in the steps A1 and B1, the entire scanning area is divided into N sectors; and in the steps A2 and B2, each time the sensor reaches the lower boundary of one sector, a temperature difference between the highest temperature and the lowest temperature of the sector is calculated, and if the temperature difference is greater than the set temperature difference threshold, the position of the urine is calculated.

Further, prior to step A, scanning is firstly conducted in the scope of the angle $\gamma$ or angle $\delta$, the lowest environment temperature in the scope of the angle $\gamma$ or angle $\delta$ is recorded, and different temperature difference thresholds are set according to different lowest environment temperatures; or the temperature difference thresholds are directly set as 3° C.

Further, the sensor has three modes comprising full-angle scanning, small-angle scanning and extended-scope scanning, within the angle $\gamma$ and the angle $\delta$; the full-angle scanning reads temperature within the entire angle $\gamma$ and angle $\delta$; each scanning area is divided into N sectors, the small-angle scanning reads temperature in the scope of a center sector and its adjacent sectors on both left and right sides; and the extended-scope scanning reads temperature in the scope of a center sector and its adjacent two sectors on both left and right sides; before the position of the urine is found for the first time, the sensor conducts the full-angle scanning; when the position of the urine is found, the sensor conducts the small-angle scanning in the sector where the urine is found and the adjacent sectors on both left and right sides; when the sensor conducts a small-angle scanning, if none of the sectors presents a temperature difference greater than the temperature difference threshold, which indicates that the position of the urine is changed, the extended-scope scanning is conducted by the sensor in the scope of the sector where the urine is originally found and adjacent two sectors on both left and right sides; and if none of the sectors presents a temperature difference greater than the temperature difference threshold during the extended-scope scanning, the sensor conducts a full-angle scanning again.

Additionally, a second technical problem to be solved by the present invention is to provide a device for automatically positioning urine in a healthy smart toilet. In this device, the urine can be positioned while it is in the air before contacting the toilet, therefore the urine can be collected without contacting the toilet, which prevents the cross-contamination between urine samples.

The present invention uses the following technical solutions in order to solve the above-mentioned technical problems.

A device for automatically positioning urine, comprising a module for automatically positioning urine, configured to determine the position of the urine according to a temperature result scanned by a non-contact temperature sensor, and calculate point coordinates of the position of the urine in a toilet.

Further, the module for automatically positioning urine comprises a first module for scanning, recording and position calculating, configured to scan and detect temperature by sector scanning within an angle γ using the non-contact temperature sensor arranged in a left or right side wall of the toilet, the non-contact temperature sensor is driven by a stepping motor, and calculate X in point coordinates (X, Y) of the position of the urine in the toilet based on the angle with the highest temperature and tangent formula; and/or a second module for scanning, recording and position calculating, configured to scan and detect temperature by sector scanning within an angle δ using the non-contact temperature sensor arranged in a front or rear side wall of the toilet, the non-contact temperature sensor is driven by the stepping motor, and calculate Y in point coordinates (X, Y) of the position of the urine in the toilet based on the angle with the highest temperature and tangent formula.

Further, the first module for scanning, recording and position calculating specifically comprises: a first module for scanning and recording, configured to: when the sensor scans within the angle γ, read temperature each time the stepping motor turns by an angle φ, and record the highest temperature value and the turning angle λ of the stepping motor at which the highest temperature value is read; and a first module for position calculating, configured to calculate the position of the urine each time the sensor reaches the boundary of the angle.

The second module for scanning, recording and position calculating specifically comprises: a second module for scanning and recording, configured to: when the sensor scans within the angle δ, read temperature each time the stepping motor turns by an angle θ, and record the highest temperature value and the turning angle ω of the stepping motor at which the highest temperature value is read; and a second module for position calculating, configured to calculate the position of the urine when the sensor reaches the boundary of the angle δ.

Further, in the first module for position calculating, the calculation method is $X=(L1/COS\ \mu)*TAN(|\gamma/2-\lambda|)$; wherein, L1 is the distance between the long shaft of the toilet and the central scanning point of the left or right side wall where the sensor is located, and μ is the included angle between a scanning plane of the sensor and the horizontal plane; and in the second module for position calculating, the calculation method is $Y=(L2/COS\ \xi)*TAN(|\delta/2-\omega|)$; wherein, L2 is the distance between the short shaft of the toilet and the central scanning point of the front or rear side wall where the sensor is located, and ξ is the included angle between a scanning plane of the sensor and the horizontal plane.

Further, in the first and second modules for scanning and recording, when the sensor reads temperature, the lowest temperature value is recorded meanwhile; and in the first and second modules for position calculating, each time the sensor reaches the boundary, a temperature difference between the highest temperature and the lowest temperature is calculated, and if the temperature difference is greater than the set temperature difference threshold, the position of the urine is calculated.

Further, in the first and second modules for scanning and recording, the entire scanning area is divided into N sectors; and in the first and second modules for position calculating, each time the sensor reaches the lower boundary of one sector, a temperature difference between the highest temperature and the lowest temperature of the sector is calculated, and if the temperature difference is greater than the set temperature difference threshold, the position of the urine is calculated.

The device for automatically positioning urine further comprises a module for setting temperature difference threshold, wherein scanning is firstly conducted in the scope of the angle γ or angle δ, the lowest environment temperature in the scope of the angle γ or angle δ is recorded, and different temperature difference thresholds are set according to different lowest environment temperatures; or the temperature difference threshold is directly set as 3° C.

The device for automatically positioning urine further comprises a module for setting temperature difference threshold, wherein scanning is firstly conducted in the scope of the angle γ or angle δ, the lowest environment temperature in the scope of the angle γ or angle δ is recorded, and different temperature difference thresholds are set according to different lowest environment temperatures; or the temperature difference threshold is directly set as 3° C.

Further, in the module for automatically positioning urine, the sensor has three modes comprising full-angle scanning, small-angle scanning and extended-scope scanning, within angle γ and angle δ; the full-angle scanning reads temperature within the entire angle γ and angle δ; each scanning area is divided into N sectors, the small-angle scanning reads temperature in the scope of a center sector and its adjacent sectors on both left and right sides; and the extended-scope scanning reads temperature in the scope of a center sector and its adjacent two sectors on both left and right sides; before the position of the urine is found for the first time, the sensor conducts the full-angle scanning; when the position of the urine is found, the sensor conducts the small-angle scanning in the scope of the sector where the urine is found and the adjacent sectors on both left and right sides; when the sensor conducts a small-angle scanning, if none of the sectors presents a temperature difference greater than the temperature difference threshold, which indicates that the position of the urine is changed, the extended-scope scanning is conducted by the sensor in the scope of the sector where the urine is originally found and adjacent two sectors on both left and right sides; and if none of the sectors presents a temperature difference greater than the temperature difference threshold during the extended-scope scanning, the sensor conducts a full-angle scanning again.

A device for automatically positioning urine comprises one or more sets of positioning assemblies in the sense of physical structure, wherein the positioning assembly comprises a non-contact temperature sensor, a stepping motor and a motor frame; the non-contact temperature sensor is fixed to the main shaft of the stepping motor, the stepping motor is fixed to the motor frame, and the motor frame is used for fixing to the toilet; and the stepping motor can drive the non-contact temperature sensor to conduct sector scanning.

The positioning assembly further comprises an optocoupler connected to the non-contact temperature sensor and used for determining a zero point of polar coordinates of the sensor.

A third technical problem to be solved by the present invention is to provide a healthy smart toilet containing a device for automatically positioning urine. In the healthy smart toilet, urine can be positioned while it is in the air before contacting the toilet, therefore the urine can be collected without contacting the toilet, which prevents the cross-contamination between urine samples.

The present invention uses the following technical solutions in order to solve the above-mentioned technical problems.

A healthy smart toilet comprises a toilet body, and further comprises the device for automatically positioning urine as described above in the section on the physical structure, wherein the device for automatically positioning urine is mounted on the toilet body, and the stepping motor can drive the non-contact temperature sensor to conduct sector scanning.

Further, two sets of the positioning assemblies are provided, one set is mounted on a front or rear side wall of the toilet body, and the other set is mounted on a left or right side wall of the toilet body.

The present invention at least has the following advantages by use of the above-mentioned designs.

1. In the present invention, point coordinates of the urine are determined by use of temperature (urine temperature, or urine temperature and environment temperature), so that the urine absorbed while being in air is used as the sample for health analysis, avoiding the cross-contamination when absorbing the urine sample from the inner surface of the toilet and thus improving the accuracy of the health data analysis.

2. By using the non-contact temperature sensor with the stepping motor to conduct sector scanning and by determining point coordinates using tangent formula, a new positioning method is provided, which is simple and practical with small error that can be neglected.

3. With two scanning areas in cooperation and using tangent formula to achieve positioning by point coordinates (X, Y), positioning accuracy is improved.

4. Positioning accuracy and positioning efficiency are improved by calculating temperature difference based on the full-angle scanning.

5. Positioning accuracy is improved by setting multiple sectors and conducting comparison calculation at the lower boundary of the sector.

6. The problem of position change of urine is solved by conducting the full-angle scanning in cooperation with the small-angle scanning or the extended-scope scanning.

7. Positioning accuracy can be improved by scanning firstly and determining the lowest environment temperature in the scanning scope, and then setting different temperature difference thresholds according to the lowest environment temperature.

BRIEF DESCRIPTION OF THE DRAWINGS

The foregoing description is merely a summary of the technical solutions of the present invention. To understand the technical means of the present invention more clearly, the present invention is further described in detail with reference to the drawings and the detailed embodiments hereinafter.

DETAILED DESCRIPTION

The present invention provides a method for automatically positioning urine in a healthy smart toilet, which mainly comprises: based on a phenomenon that a temperature of urine is higher than an environment temperature, conducting scans for the urine by a non-contact temperature sensor when the toilet is in use, determining a position of the urine according to a temperature result scanned, and calculating the coordinates of the position points of the urine in the toilet. By this method, urine can be positioned while it is in the air, therefore the urine can be collected without contacting the toilet. This method prevents the cross-contamination between urine samples and improves the accuracy of the health data analysis. Preferably, the non-contact temperature sensor is an infrared temperature sensor.

According to the temperature positioning principle above, either a horizontal and vertical straight-line scanning mode, or a sector scanning mode can be used.

Figure 1:
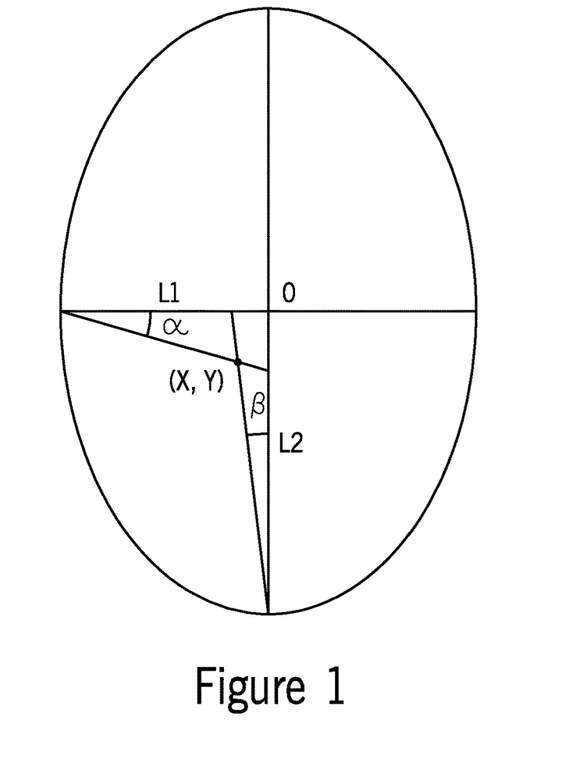
FIG. 1 is a schematic diagram of the position of urine in a toilet.
Figure 13A:
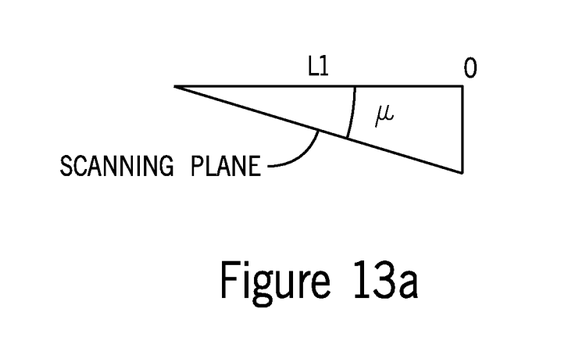
FIGS. 13a and 13b are schematic diagrams of included angles between a scanning plane and a horizontal plane.
Figure 13B:
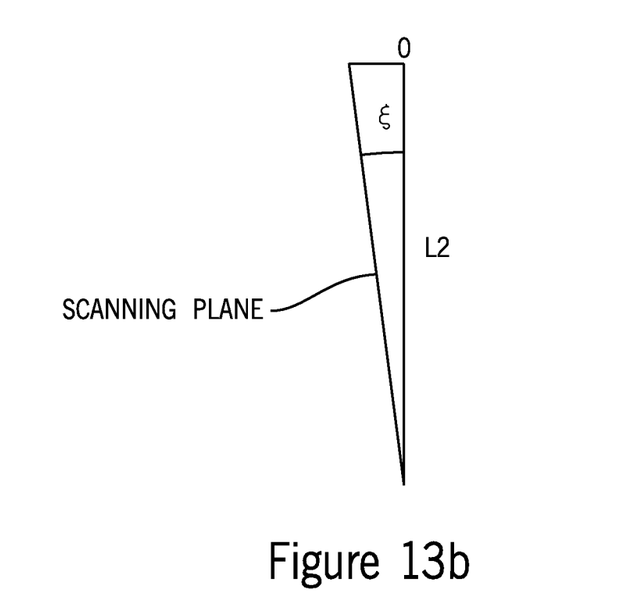

As shown in FIG. 1, the sector scanning mode mainly comprises scanning and detecting temperature by sector scanning within an angle γ using a non-contact temperature sensor arranged in a left or right side wall of the toilet and driven by a stepping motor, and calculating, based on the angle with the highest temperature and tangent formula, X in point coordinates (X, Y) of the position of the urine in the toilet; the Y value can be left undetermined, and the urine can be collected directly by a urine receiving device moving along a long shaft of the toilet. In order to further determine the position of urine more accurately, the Y in the coordinate point of the urine can be determined, the method for determining Y is similar to the method for determining X, which comprises scanning and detecting temperature by sector scanning within an angle δ using a non-contact temperature sensor arranged in a front or rear side wall of the toilet and driven by a stepping motor, and calculating, based on the angle with the highest temperature and tangent formula, the Y value in the point coordinates (X, Y) of the position of urine in the toilet. In the point coordinates (X, Y), $X=(L1/COS\ \mu)*TAN(\alpha)$, $Y=(L2/COS\ \xi)*TAN(\beta)$, wherein L1 is the distance between the long shaft of the toilet and the central scanning point of the left or right side wall where the sensor is located, L2 is a distance between a short shaft of the toilet and a central scanning point of the front or rear side wall where the sensor is located, $\mu$ and $\xi$ are the angles between a scanning plane of the sensor and a horizontal plane (as shown in FIGS. 13a and 13b). The error in the calculation formula is small and can be neglected. The $\mu$ and $\xi$ above can be 0 degree.

Preferably, two sensors are used, one sensor is arranged at a center position of the left or right side wall of the toilet to calculate the X in the point coordinates (X, Y), and the other sensor is arranged at a center position of the front or rear side wall of the toilet to calculate the Y in the point coordinates (X, Y). The positions above are only preferred positions, and the two sensors can also be arranged at other positions.

Detailed description is conducted by taking the sector scanning mode as an example.

Embodiment 1

Figure 2:
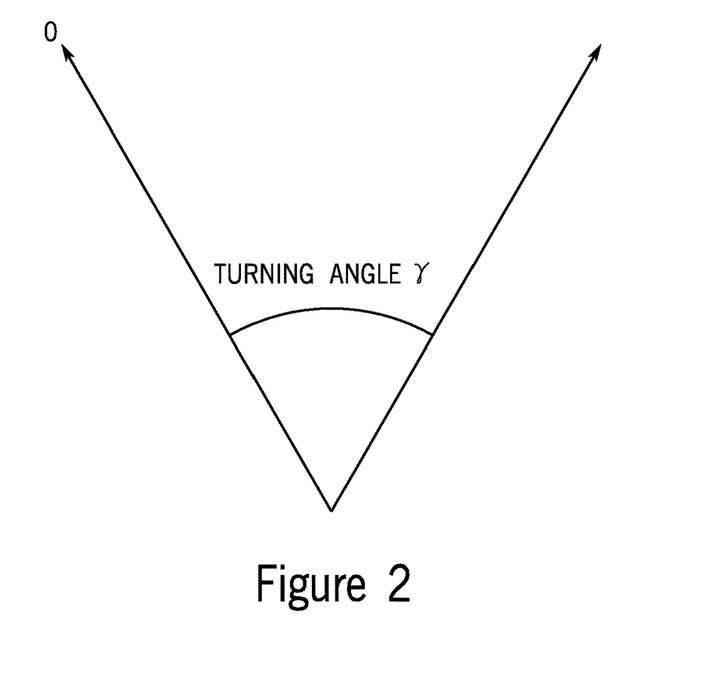
FIG. 2 is a schematic diagram of a sector scanning scope.

A sensor is mounted and fixed on the main shaft of a stepping motor, the sensor scans with the main shaft of the stepping motor within an angle $\gamma$, as shown in FIG. 2. Preferably, the scanning is conducted in a scope of 60 degrees. When the sensor scans within the angle $\gamma$, each time the stepping motor turns by an angle $\varphi$, the temperature is read by the sensor. The highest temperature value and the turning angle $\lambda$ of the stepping motor at which the highest temperature value is read are recorded, wherein $\lambda$ is equal to an integral multiple of the angle $\varphi$, and a preferred value of the angle $\varphi$ is 0.04*frequency*stepping angle.

Figure 3:
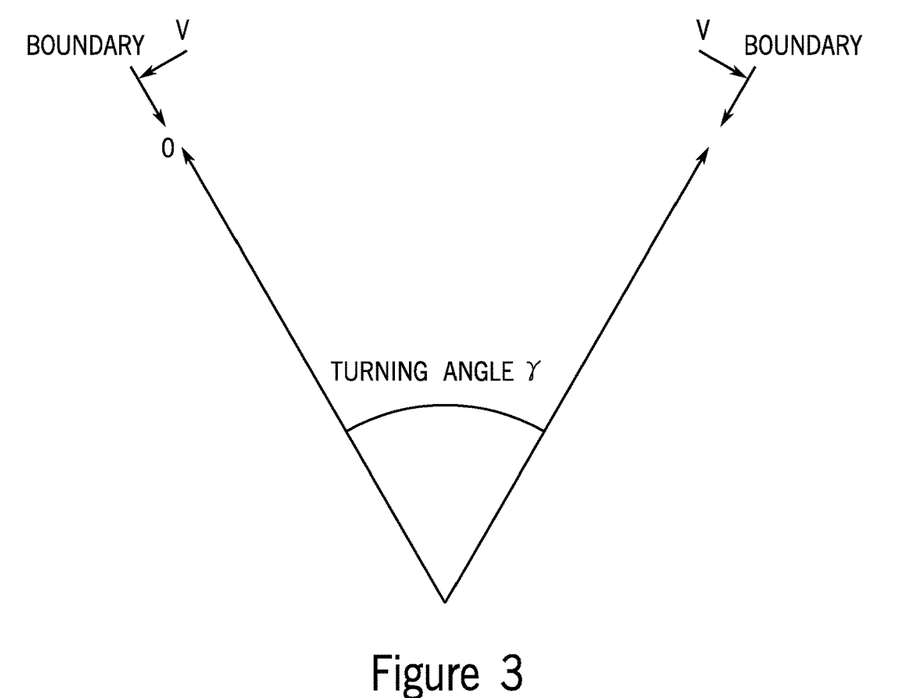
FIG. 3 is a schematic diagram of scanning boundaries (clockwise and counterclockwise)

The position of the urine is calculated each time the sensor reaches the boundary of the angle $\gamma$, as shown in FIG. 3. $\alpha=|\gamma/2-\lambda|$, and $X=(L1/COS\ \mu)*TAN(|\gamma/2-\lambda|)$. Similarly, it can be calculated that $\beta=|\delta/2-\omega|$, and $Y=(L2/COS\ \xi)*TAN(|\delta/2-\omega|)$.

Embodiment 2

A sensor is mounted and fixed on the main shaft of a stepping motor, the sensor scans with the main shaft of the stepping motor within an angle $\gamma$, as shown in FIG. 2.

When the sensor scans within the angle $\gamma$, the temperature is read by the sensor each time the stepping motor turns by an angle $\varphi$, and the highest temperature value, the lowest temperature value and the turning angle $\lambda$ of the stepping motor at which the highest temperature value is read are recorded.

A temperature difference between the highest temperature and the lowest temperature of the sector is calculated each time the sensor reaches the boundary of the angle $\gamma$, as shown in FIG. 3. If the temperature difference is greater than 3° C., the position of the urine is calculated. Experiments show that the accuracy of calculating position of urine is higher when the temperature difference is greater than 3° C. $\alpha=|\gamma/2-\lambda|$, and $X=(L1/COS\ \mu)*TAN(|\gamma/2-\lambda|)$. Similarly, it can be calculated that $\beta=|\delta/2-\omega|$, and $Y=(L2/COS\ \xi)*TAN(|\delta/2-\omega|)$.

Embodiment 3

A sensor is mounted and fixed on the main shaft of a stepping motor, the sensor scans with the main shaft of the stepping motor within an angle $\gamma$, as shown in FIG. 2.

Figure 4:
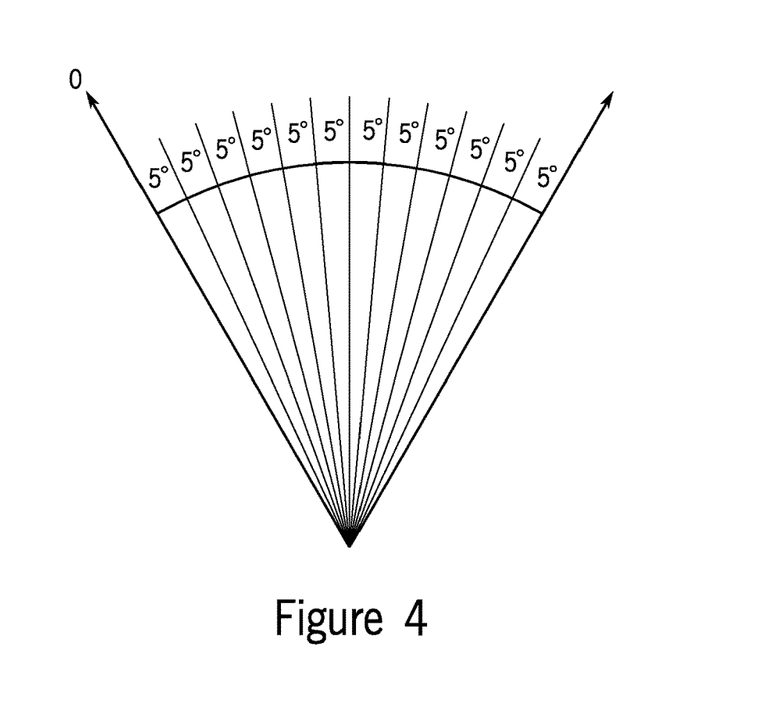
FIG. 4 is a schematic diagram of sector division.

In the angle $\gamma$, every 5 degrees are defined as one sector, and the entire angle $\gamma$ is divided into N sectors, as shown in FIG. 4. Experiments show that the calculation efficiency is higher when one sector includes 5 degrees.

When the sensor scans within the angle $\gamma$, temperature is read by the sensor each time the stepping motor turns by an angle $\varphi$, and the highest temperature value, the lowest temperature value and the turning angle $\lambda$ of the stepping motor at which the highest temperature value is read are recorded.

Figure 5:
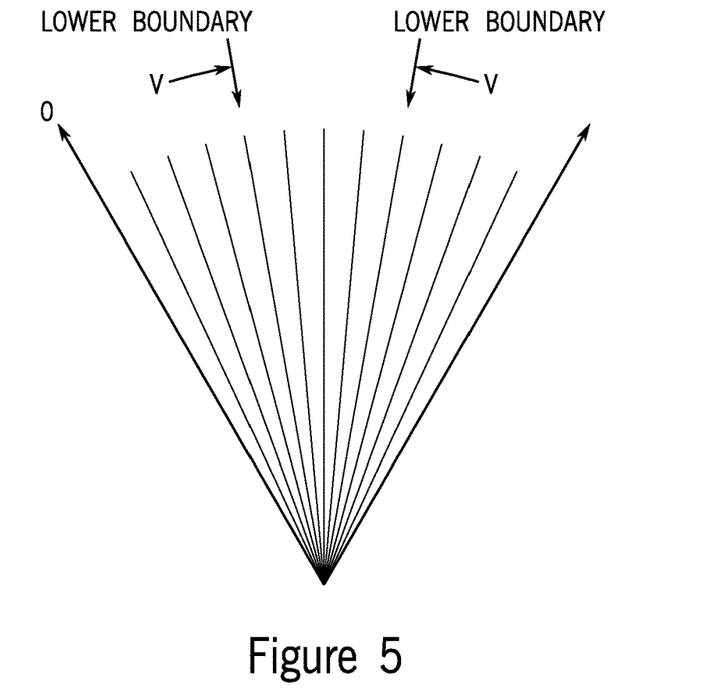
FIG. 5 is a schematic diagram of lower boundaries of the sectors (clockwise and counterclockwise)

A temperature difference between the highest temperature and the lowest temperature of the sector is calculated each time the sensor reaches the lower boundary of a sector, as shown in FIG. 5. If the temperature difference is greater than 3° C., the position of the urine is calculated. $\alpha=|\gamma/2-\lambda|$, and $X=(L1/COS\ \mu)*TAN(|\gamma/2-\lambda|)$. Similarly, it can be calculated that $\beta=|\delta/2-\omega|$, and $Y=(L2/COS\ \xi)*TAN(|\delta/2-\omega|)$.

When the position of the urine is changed, the sensor needs to re-determine the position of the urine.

Figure 6:
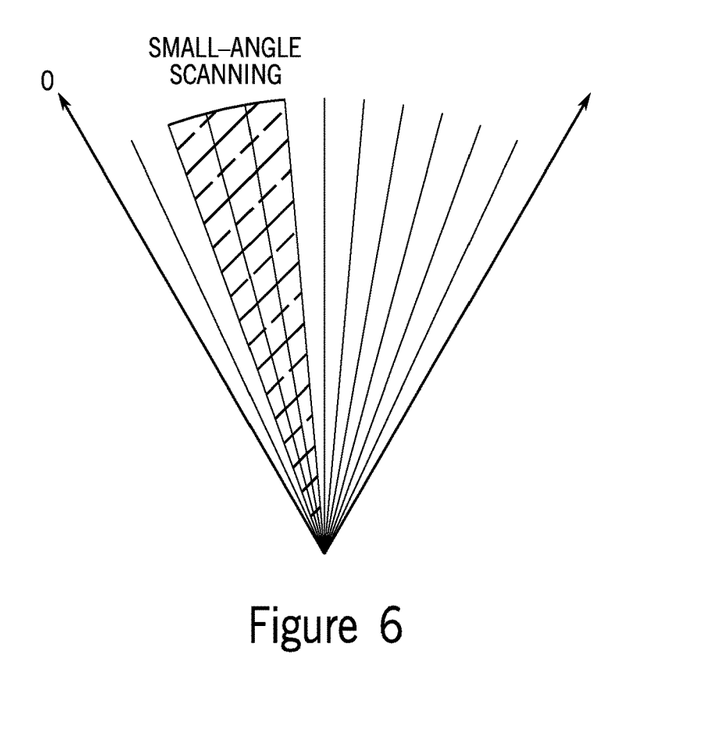
FIG. 6 is a schematic diagram of small-angle scanning.
Figure 7:
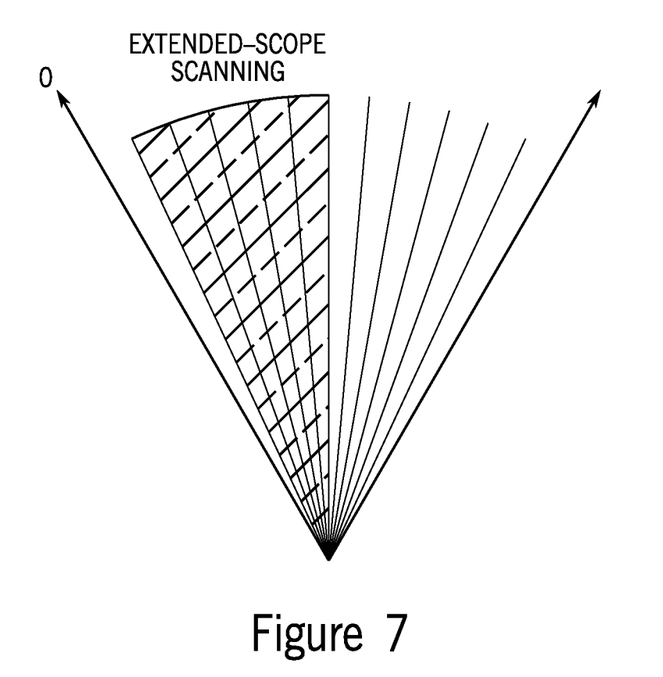
FIG. 7 is a schematic diagram of extended-scope scanning.

The sensor has three modes comprising full-angle scanning, small-angle scanning and extended-scope scanning, in the angle $\gamma$. The full-angle scanning reads the temperature in the entire angle $\gamma$. The small-angle scanning reads temperature in the scope of a center sector and its adjacent sectors on both left and right sides, as shown in FIG. 6. The extended-scope scanning reads temperature in the scope of a center sector and its adjacent two sectors on both left and right sides, as shown in FIG. 7.

Before the position of the urine is found for the first time, the sensor conducts the full-angle scanning.

When the position of the urine is found, the sensor conducts the small-angle scanning in the scope of the sector where the urine is found and the adjacent sectors on both left and right sides.

When the sensor conducts the small-angle scanning, if none of the sectors presents a temperature difference greater than the temperature difference threshold, which indicates that the position of the urine is changed, the sensor conducts the extended-scope scanning in the scope of the center sector where the urine is originally found and adjacent two sectors on both left and right sides.

If none of the sectors presents a temperature difference greater than the temperature difference threshold during the extended-scope scanning, the sensor conducts a full-angle scanning again.

Figure 8:
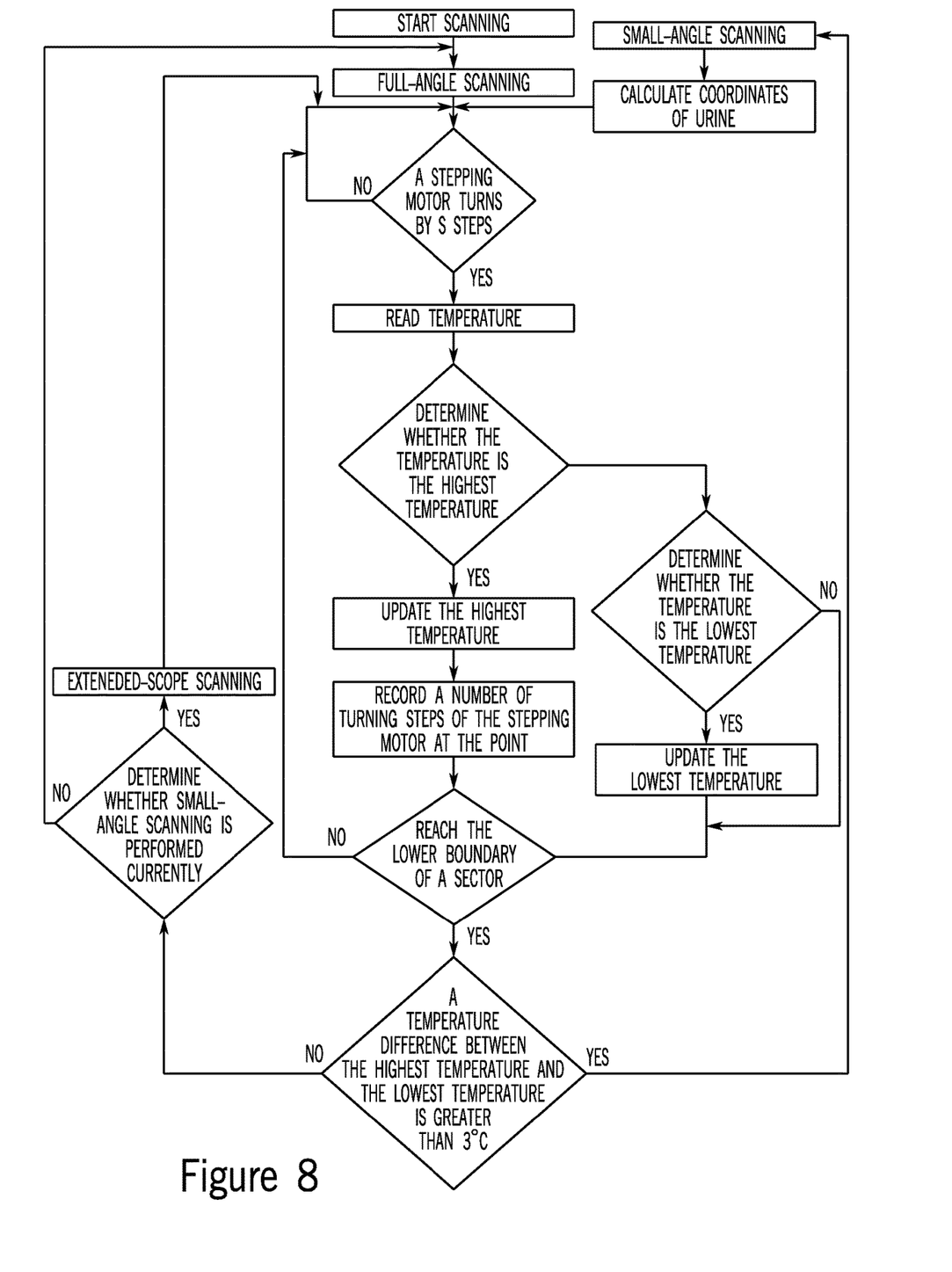
FIG. 8 is a control flowchart of a method according to a third embodiment.

A control flowchart of the entire method is shown in FIG. 8.

Embodiment 4

A sensor is mounted and fixed on the main shaft of a stepping motor, the sensor scans with the main shaft of the stepping motor within an angle $\gamma$, as shown in FIG. 2.

When the sensor scans within the angle $\gamma$ for the first time, temperature is read by the sensor each time the stepping motor turns by an angle $\varphi$, and the lowest temperature value is recorded. Environment temperature is calculated when the boundary of the angle $\gamma$ is reached, and the environment temperature is the lowest temperature. Different temperature difference thresholds are set according to different environment temperatures.

When the sensor scans within the angle $\gamma$ for the second and subsequent times, temperature is read once by the sensor each time the stepping motor turns by an angle $\varphi$, and the highest temperature value, the lowest temperature value and a turning angle $\lambda$ of the stepping motor at which the highest temperature value is read are recorded.

In the angle γ, every 5 degrees are defined as one sector, and the entire angle γ is divided into N sectors, as shown in FIG. 4.

A temperature difference between the highest temperature and the lowest temperature of the sector is calculated when the sensor reaches the lower boundary of a sector, as shown in FIG. 5. If the temperature difference is greater than the temperature difference threshold, the position of the urine is calculated. $\alpha=|\gamma/2-\lambda|$, and $X=(L1/COS\ \mu)*TAN(|\gamma/2-\lambda|)$. Similarly, it can be calculated that $\beta=|\delta/2-\omega|$, and $Y=(L2/COS\ \xi)*TAN(|\delta/2-\omega|)$.

When the position of the urine is changed, the sensor needs to re-determine the position of the urine.

The sensor has three modes comprising full-angle scanning, small-angle scanning and extended-scope scanning in the angle γ. The full-angle scanning reads temperature in the entire angle γ. The small-angle scanning reads temperature in the scope of a center sector and its adjacent sectors on both left and right sides, as shown in FIG. 6. The extended-scope scanning reads temperature in the scope of a center sector and its adjacent two sectors on both left and right sides, as shown in FIG. 7.

Before the position of the urine is found for the first time, the sensor conducts the full-angle scanning.

When the position of the urine is found, the sensor conducts the small-angle scanning in the scope of the sector where the urine is found and the adjacent sectors on both left and right sides.

When the sensor conducts the small-angle scanning, if none of the sectors presents a temperature difference greater than the temperature difference threshold, which indicates that the position of the urine is changed, the sensor conducts the extended-scope scanning in the scope of the sector where the urine is originally found and the adjacent two sectors on both left and right sides.

If none of the sectors presents a temperature difference greater than the temperature difference threshold during the extended-scope scanning, the sensor conducts a full-angle scanning again.

Figure 9:
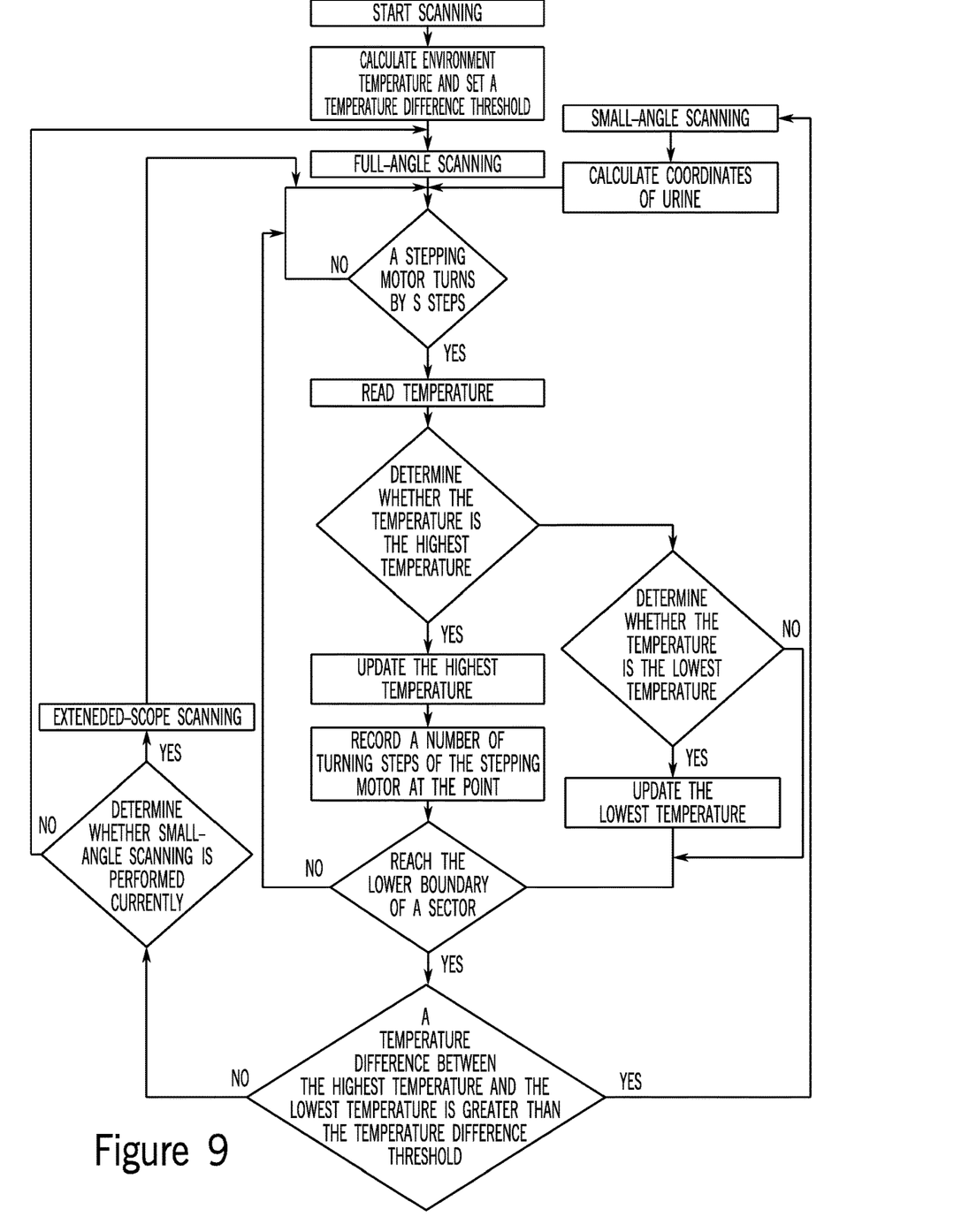
FIG. 9 is a control flowchart of a method according to a fourth embodiment.

A control flowchart of the entire method is shown in FIG. 9.

Embodiment 5 (as Shown in FIGS. 1 to 9)

A device for automatically positioning urine for a healthy smart toilet according to the present invention, in a sense of virtual module structure, the device comprises a module for automatically positioning urine configured to determine the position of urine according to a temperature result scanned by a non-contact temperature sensor and calculate point coordinates of the position of the urine in the toilet.

The above module for automatically positioning urine comprises:

a first module for scanning, recording and position calculating, configured to scan and detect temperature by sector scanning within an angle γ using a non-contact temperature sensor arranged in a left or right side wall of the toilet driven by a stepping motor, and calculate, based on the angle with the highest temperature and tangent formula, X in point coordinates (X, Y) of the position of the urine in the toilet; and/or a second module for scanning, recording and position calculating, configured to scan and detect temperature by sector scanning within an angle δ using the non-contact temperature sensor arranged in a front or rear side wall of the toilet and driven by a stepping motor, and calculate, based on the angle with the highest temperature and tangent formula, Y in point coordinates (X, Y) of the position of the urine in the toilet.

The above first module for scanning, recording and position calculating specifically comprises: a first module for scanning and recording, configured to read temperature by the sensor when the sensor scans within the angle γ each time the stepping motor turns by an angle φ, and to record the highest temperature value and the turning angle λ of the stepping motor at which the highest temperature value is read; and a first module for position calculating, configured to calculate the position of the urine when the sensor reaches the boundary of the angle γ; and the above second module for scanning, recording and position calculating specifically comprises: a second module for scanning and recording, configured to read temperature by the sensor when the sensor scans within the angle δ each time the stepping motor turns by an angle θ, and to record the highest temperature value and the turning angle ω of the stepping motor at which the highest temperature value is read; and a second module for position calculating, configured to calculate the position of the urine when the sensor reaches the boundary of the angle δ.

In the first module for position calculating of the first module for scanning, recording and position calculating, the calculation method is: $X=(L1/COS\ \mu)*TAN(|\gamma/2-\lambda|)$; wherein, L1 is the distance between the long shaft of the toilet and the central scanning point of the left or right side wall where the sensor is located.

In the second module for position calculating of the second module for scanning, recording and position calculating, the calculation method is $Y=(L2/COS\ \xi)*TAN(|\delta/2-\omega|)$; wherein, L2 is the distance between the short shaft of the toilet and the central scanning point of the front or rear side wall where the sensor is located.

Preferably, in the first and second modules for scanning and recording, when the sensor reads temperature, the lowest temperature value is recorded meanwhile; and in the first and second modules for position calculating, each time the sensor reaches the boundary, a temperature difference between the highest temperature and the lowest temperature is calculated, and if the temperature difference is greater than a set temperature difference threshold, the position of the urine is calculated.

Preferably, in the first and second modules for scanning and recording, the entire scanning area is divided into N sectors; and in the first and second modules for position calculating, each time the sensor reaches the lower boundary of one sector, a temperature difference between the highest temperature and the lowest temperature of the sector is calculated, and if the temperature difference is greater than the set temperature difference threshold, the position of the urine is calculated.

Preferably, the device for automatically positioning urine further comprises a module for setting temperature difference threshold, wherein scanning is firstly conducted in the scope of the angle γ or angle δ, the lowest environment temperature in the scope of the angle γ or angle δ is recorded, and different temperature difference thresholds are set according to different lowest environment temperatures; or the temperature difference threshold is directly set as 3° C.

Preferably, in the module for automatically positioning urine, the sensor has three modes comprising full-angle scanning, small-angle scanning and extended-scope scanning in the angle γ and angle δ; the full-angle scanning reads temperature within the entire angle γ and angle δ; Each scanning area is divided into N sectors, the small-angle scanning reads temperature in the scope of a center sector and its adjacent sectors on both left and right sides; and the extended-scope scanning reads temperature in the scope of a center sector and its adjacent two sectors on both left and right sides; before the position of the urine is found for the first time, the sensor conducts the full-angle scanning; when the position of the urine is found, the sensor conducts the small-angle scanning in the scope of the sector where the urine is found and the adjacent sectors on both left and right sides; when the sensor conducts a small-angle scanning, if none of the sectors presents a temperature difference greater than the temperature difference threshold, which indicates that the position of the urine is changed, the extended-scope scanning is conducted by the sensor in the scope of the sector where the urine is originally found and adjacent two sectors on both left and right sides; and if none of the sectors presents a temperature difference greater than the temperature difference threshold during the extended-scope scanning, the sensor conducts a full-angle scanning again.

Embodiment 6

Figure 10:
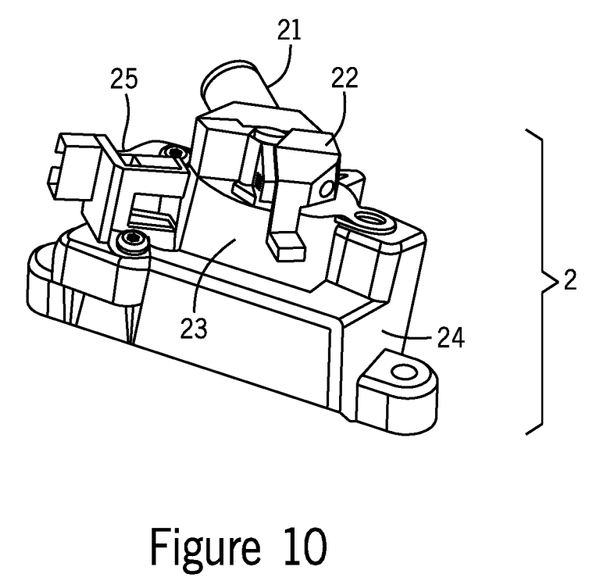
FIG. 10 and FIG. 11 are schematic diagrams of physical structures of a device for automatically positioning urine at different angles.
Figure 11:
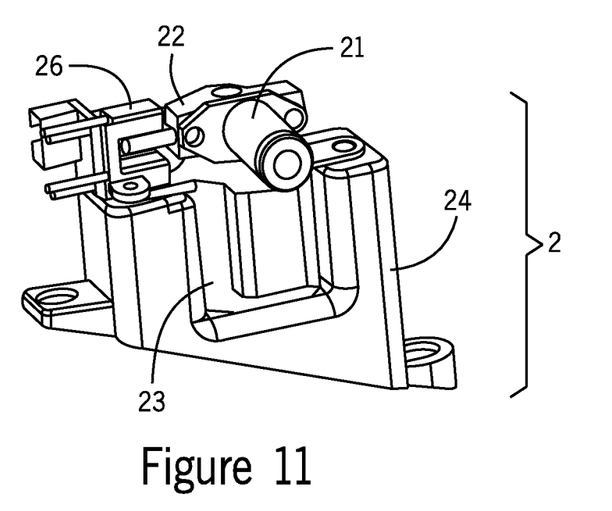

As shown in FIGS. 10 and 11, in a sense of physical structure, a device for automatically positioning urine according to the present invention comprises one or more sets of positioning assemblies 2; wherein the positioning assembly 2 comprises a non-contact temperature sensor 21, a stepping motor 23 and a motor frame 24; the non-contact temperature sensor may be an infrared temperature sensor, and may be fixed to the main shaft of the stepping motor 23 through a sensor fixing part 22, the stepping motor 23 is fixed to the motor frame 24, and the motor frame 24 is used for fixing to the toilet; and the stepping motor 23 can drive the non-contact temperature sensor 21 to conduct sector scanning.

The above positioning assembly 2 further comprises an optocoupler 25 connected to the non-contact temperature sensor 21 and used for determining a zero point of polar coordinates of the sensor.

Embodiment 7

Figure 12:
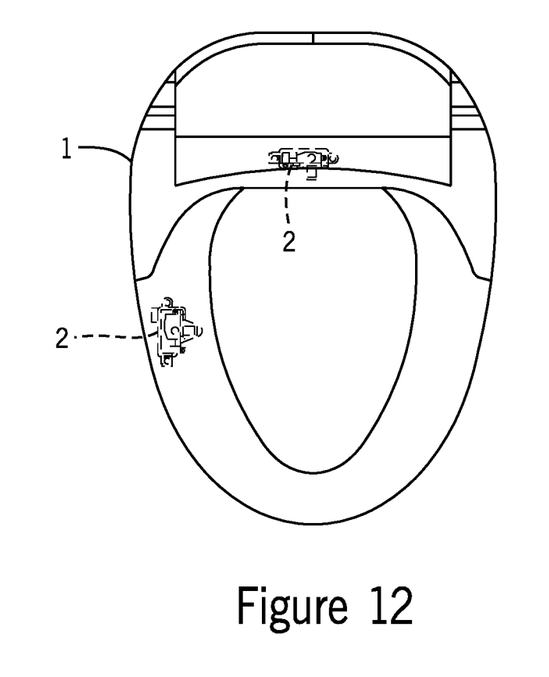
FIG. 12 is a schematic structure diagram of a healthy smart toilet containing the device for automatically positioning urine.

As shown in FIG. 12, a healthy smart toilet according to the present invention comprises a toilet body 1, and further comprises a device for automatically positioning urine, which is mounted on the toilet body 1, one or more sets of the positioning assemblies 2 as described in the embodiment 6 are used in the device for automatically positioning urine. The stepping motor 23 can drive the non-contact temperature sensor 21 to conduct sector scanning, and a certain included angle may be formed between a scanning plane and a horizontal plane, or a horizontal scanning may be directly conducted.

One set of the positioning assembly 2 may be provided, which is mounted on a left or right side wall of the toilet body 1, and more preferably, two sets of the positioning assemblies 2 may be provided, one set is mounted on a front or rear side wall of the toilet body 1, and the other set is mounted on the left or right side wall of the toilet body 1.

The foregoing description is merely preferred embodiments of the present invention, but is not intended to limit the present invention in any form, and any simple amendments, equivalent changes or modifications made by those skilled in the art using the technical contents disclosed above shall all fall within the protection scope of the present invention.

What is claimed is:

1. A toilet comprising:
a module including a sensor that is configured to determine a characteristic of urine with the urine in a non-contact position relative to a surface of the toilet, wherein the module is configured to calculate point coordinates of the non-contact position of the urine based on the characteristic.

2. The toilet of claim 1, wherein the characteristic is a temperature of the urine, and the sensor is a temperature sensor configured to detect the temperature of the urine in the non-contact position.

3. The toilet of claim 1, wherein the sensor is coupled to a stepping motor, such that the sensor is configured to rotate and scan an area of the toilet to detect a temperature.

4. The toilet of claim 1, wherein the sensor is an infrared temperature sensor.

5. The toilet of claim 1, wherein the sensor is arranged in a side wall of the toilet.

6. The toilet of claim 1, wherein the sensor is a first sensor arranged at a left side wall or a right side wall of the toilet, and wherein the toilet further comprises a second sensor arranged at a front side wall or a rear side wall of the toilet.

7. The toilet of claim 6, wherein the first sensor is configured to facilitate calculation of a first point coordinate of the non-contact position of the urine and the second sensor is configured to facilitate calculation of a second point coordinate of the non-contact position of the urine.

8. A method of detecting a position of urine in a toilet, the method comprising:
sensing a characteristic of the urine in a non-contact position with a surface of the toilet with a sensor of a module of the toilet; and
calculating point coordinates of the non-contact position of the urine with the module based on the characteristic.

9. The method of claim 8, wherein the characteristic is a temperature such that the sensor senses the temperature of the urine in the non-contact position.

10. The method of claim 8, wherein the sensor is coupled to a stepping motor, and wherein sensing the characteristic includes rotating the sensor with the stepping motor to scan an area of the toilet.

11. The method of claim 8, wherein the sensor is an infrared temperature sensor.

12. The method of claim 8, wherein the sensor is arranged in a side wall of the toilet.

13. The method of claim 8, wherein the sensor is a first sensor and the toilet further comprises a second sensor, and wherein calculating the point coordinates of the non-contact position of the urine includes determining a first point coordinate using the first sensor and determining a second point coordinate using the second sensor.

14. The method of claim 13, wherein the first sensor is arranged at a left side wall or a right side wall of the toilet, and wherein the second sensor is arranged at a front side wall or a rear side wall of the toilet.

15. A method of detecting urine using a toilet, the method comprising:
sensing a temperature of the urine in a position relative to the toilet using a sensor of a module of the toilet;
sensing an environment temperature associated with a portion of the toilet using the module; and
calculating point coordinates of the position of the urine based on the environment temperature and the temperature of the urine.

16. The method of claim 15, wherein the position is a non-contact position with a surface of the toilet.

17. The method of claim 15, wherein the sensor is coupled to a stepping motor, and wherein sensing the temperature includes rotating the sensor with the stepping motor to scan an area of the toilet.

18. The method of claim 15, wherein the sensor is an infrared temperature sensor.

19. The method of claim 15, wherein the sensor is arranged in a side wall of the toilet.

20. The method of claim 15, wherein calculating the point coordinates of the position of the urine comprises:
   calculating a temperature difference between the environment temperature and the temperature of the urine; and
   comparing the temperature difference to a temperature difference threshold.

* * * * *